US012594161B2

(12) United States Patent
Quill et al.

(10) Patent No.: US 12,594,161 B2
(45) Date of Patent: \*Apr. 7, 2026

(54) SYSTEMS AND METHODS FOR PREDICTABLE COMMISSURAL ALIGNMENT OF A REPLACEMENT HEART VALVE

(71) Applicant: ANTERIS TECHNOLOGIES CORPORATION, Eagan, MN (US)

(72) Inventors: Jason L. Quill, Forest Lake, MN (US); Dannah Dean, Minnetonka, MN (US); Cameron James Albin Murto, Saint Michael, MN (US); Edward James Anderson, Maple Grove, MN (US); Brad James Traeger, Eden Prairie, MN (US); Payton Kristine Parmett, Lakeville, MN (US); Nicholas Weldon Pensa, Minneapolis, MN (US); Joseph Allen Duerr, Andover, MN (US)

(73) Assignee: Anteris Technologies Corporation, Eagan, MN (US)

( \* ) Notice: Subject to any disclaimer, the term of this patent is extended or adjusted under 35 U.S.C. 154(b) by 298 days.

This patent is subject to a terminal disclaimer.

(21) Appl. No.: 18/393,475

(22) Filed: Dec. 21, 2023

(65) Prior Publication Data

US 2024/0122706 A1 Apr. 18, 2024

Related U.S. Application Data

(63) Continuation of application No. 18/104,502, filed on Feb. 1, 2023, now Pat. No. 11,883,286, which is a
(Continued)

(51) Int. Cl.
*A61M 25/10* (2013.01)
*A61F 2/24* (2006.01)

(52) U.S. Cl.
CPC .......... *A61F 2/2433* (2013.01); *A61F 2/2418* (2013.01); *A61M 25/10* (2013.01);
(Continued)

(58) Field of Classification Search
CPC ............ A61F 2002/9583; A61F 2/2433; A61F 2/2436; A61F 2/9517; A61F 2/2427;
(Continued)

(56) References Cited

U.S. PATENT DOCUMENTS 6,027,510 A 2/2000 Alt
6,878,151 B2 4/2005 Carrison et al.
(Continued)

FOREIGN PATENT DOCUMENTS

CA 2768506 A1 \* 1/2011 ........ A61M 25/0075
CN 103096838 A \* 5/2013 ........... A61F 2/9517
(Continued)

OTHER PUBLICATIONS

Extended European Search Report in European Appln. No. 22842742. 3, mailed on Jun. 20, 2025, 10 pages.
(Continued)

*Primary Examiner* — Seema Mathew
(74) *Attorney, Agent, or Firm* — Fish & Richardson P.C.

(57) ABSTRACT

A replacement heart valve prosthesis is loaded onto a balloon mounted onto a balloon shaft of a catheter system. The balloon shaft is rotatably engaged with an actuator on the handle of the catheter system. Rotation of the actuator by a first amount in a first direction permits rotation of the heart valve prosthesis by a known amount during the procedure so that alignment of the commissures of the replacement valve with the commissures of the existing valve can be predictably achieved.

20 Claims, 7 Drawing Sheets

Related U.S. Application Data continuation of application No. PCT/US2022/036781, filed on Jul. 12, 2022.

(60) Provisional application No. 63/220,989, filed on Jul. 12, 2021.

(52) U.S. Cl.
CPC ................ *A61F 2250/0097* (2013.01); *A61M 2025/1075* (2013.01); *A61M 2025/1079* (2013.01); *A61M 2205/0216* (2013.01)

(58) Field of Classification Search
CPC .. A61F 2/95; A61F 2/966; A61F 2/958; A61F 2/243; A61F 2/82; A61M 2025/0681; A61M 2025/105; A61M 25/10; A61M 25/1002; A61M 27/002
See application file for complete search history.

(56) References Cited

U.S. PATENT DOCUMENTS

| | | | |
|---|---|---|---|
| 9,205,172 | B2 | 12/2015 | Leonard Neethling et al. |
| 9,770,575 | B2 | 9/2017 | Wesselmann et al. |
| 10,238,495 | B2 | 3/2019 | Marsot et al. |
| 10,398,550 | B2 | 9/2019 | Chalekian et al. |
| 10,441,419 | B2 | 10/2019 | Le et al. |
| 10,517,723 | B2 | 12/2019 | Knippel et al. |
| 10,624,740 | B2 | 4/2020 | Perszyk |
| 10,631,986 | B2 | 4/2020 | Copeland et al. |
| 10,758,352 | B2 | 9/2020 | Wilson et al. |
| 10,799,676 | B2 | 10/2020 | Khuu et al. |
| 10,898,324 | B2 | 1/2021 | Morrissey et al. |
| 10,905,550 | B2 * | 2/2021 | Lally .................... A61F 2/2436 |
| 11,007,056 | B2 * | 5/2021 | Morrissey ............ A61F 2/2436 |
| 11,219,746 | B2 | 1/2022 | Khuu et al. |
| 11,298,252 | B2 * | 4/2022 | Bourang ................ A61F 2/856 |
| 11,311,399 | B2 * | 4/2022 | Desrosiers ............ A61F 2/2436 |
| 11,464,631 | B2 * | 10/2022 | Kerr ...................... A61M 29/02 |
| 11,612,385 | B2 * | 3/2023 | Nae .......................... A61F 2/966 604/9 |
| 11,648,107 | B2 | 5/2023 | Neethling et al. |
| 12,390,329 | B1 * | 8/2025 | Quill .................... A61F 2/2433 |
| 2004/0102791 | A1 | 5/2004 | Murray, III |
| 2005/0080474 | A1 | 4/2005 | Andreas et al. |
| 2011/0015616 | A1 | 1/2011 | Straubinger et al. |
| 2011/0190778 | A1 | 8/2011 | Arpasi et al. |
| 2013/0297011 | A1 | 11/2013 | Morris et al. |
| 2017/0100250 | A1 | 4/2017 | Marsot et al. |
| 2018/0153696 | A1 | 6/2018 | Albitov et al. |
| 2018/0214267 | A1 | 8/2018 | Lally et al. |
| 2019/0290425 | A1 | 9/2019 | Dehdashtian et al. |
| 2020/0060820 | A1 | 2/2020 | Ben-Zvi et al. |
| 2020/0108234 | A1 | 4/2020 | Sanati et al. |
| 2020/0383780 | A1 * | 12/2020 | Chang ................... A61F 2/2433 |
| 2022/0000445 | A1 | 1/2022 | Datta et al. |
| 2022/0008200 | A1 * | 1/2022 | Popp ..................... A61F 2/2439 |
| 2022/0031455 | A1 | 2/2022 | Straubinge et al. |
| 2022/0047267 | A1 | 2/2022 | Johnston et al. |
| 2022/0226114 | A1 * | 7/2022 | Hou ...................... A61F 2/2433 |
| 2022/0280298 | A1 * | 9/2022 | Schwarcz ............ A61F 2/2433 |
| 2022/0338987 | A1 * | 10/2022 | Schwarcz ............ A61F 2/2418 |
| 2023/0255654 | A1 * | 8/2023 | Drake .................... A61B 17/32 606/1 |
| 2023/0277809 | A1 * | 9/2023 | Desrosiers ............ A61M 25/01 600/585 |
| 2024/0122706 | A1 * | 4/2024 | Quill ..................... A61F 2/2418 |
| 2024/0390139 | A1 * | 11/2024 | Hummel ............... A61F 2/2418 |
| 2025/0127618 | A1 * | 4/2025 | Govek .................. A61F 2/2433 |
| 2025/0128027 | A1 * | 4/2025 | Govek .............. A61M 25/0147 |
| 2025/0205049 | A1 * | 6/2025 | Ness ..................... A61F 2/2433 |
| 2025/0213360 | A1 * | 7/2025 | Ness ..................... A61F 2/2418 |
| 2025/0241752 | A1 * | 7/2025 | Morrissey ............ A61F 2/2433 |
| 2025/0248813 | A1 * | 8/2025 | Govek .............. A61M 25/0668 |
| 2025/0262050 | A1 * | 8/2025 | Govek .................. A61F 2/2433 |
| 2025/0331986 | A1 * | 10/2025 | Quill ..................... A61F 2/2433 |

FOREIGN PATENT DOCUMENTS

| | | | | | |
|---|---|---|---|---|---|
| EP | | 4410350 | A1 * | 8/2024 | ........ A61M 25/0147 |
| JP | | 2010-517622 | A | 5/2010 | |
| JP | | 2017-530814 | A5 | 8/2018 | |
| JP | | 2020-062399 | A | 4/2020 | |
| JP | | 2020-505176 | A5 | 3/2021 | |
| JP | | 2021-511123 | A | 5/2021 | |
| WO | WO-2014026028 | A1 * | 2/2014 | | ........ A61B 17/3478 |
| WO | WO 2021040547 | A1 | 3/2021 | | |
| WO | WO 2022010954 | | 1/2022 | | |
| WO | WO 2022010958 | | 1/2022 | | |

OTHER PUBLICATIONS

International Preliminary Report on Patentability in International Appln. No. PCT/US2022/036781, mailed on Jan. 25, 2024, 6 pages.
Search Report and Written Opinion for related PCT Application No. PCT/US2022/036780 mailed Nov. 3, 2022 (7 pages).
Search Report and Written Opinion for related PCT Application No. PCT/US2022/036781 mailed Nov. 3, 2022 (11 pages).

* cited by examiner

SYSTEMS AND METHODS FOR PREDICTABLE COMMISSURAL ALIGNMENT OF A REPLACEMENT HEART VALVE

CROSS-REFERENCE TO RELATED APPLICATIONS

The present disclosure is a continuation of U.S. application Ser. No. 18/104,502 filed on Feb. 1, 2023, which is a continuation of PCT/US2022/036781 filed Jul. 12, 2022, which claims priority to U.S. Provisional Application No. 63/220,989 filed Jul. 12, 2021, the contents of which are hereby incorporated by reference herein in their entirety.

BACKGROUND OF THE INVENTION

The present disclosure relates to novel and advantageous systems and methods to assist a practitioner during deployment with alignment of the commissural posts on the valve prosthesis with the existing commissures of the patient's current valve, which may be a native valve or a previously replaced valve.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Transcatheter valve replacement (TVR) is a minimally invasive heart procedure to repair or replace a valve of the heart by using an implantable valve prosthesis delivered to the patient's native valve via a catheter. The implantable valve prosthesis typically comprises an expandable frame with leaflets attached to the interior of the expandable frame. The prosthetic leaflets are intended to mimic the action of healthier native leaflets. Transcatheter valve replacement prostheses have been developed for the aortic, mitral, and tricuspid valves. TVR procedures typically involve the introduction of a catheter to the patient's vasculature transfemorally, where the valve prosthesis is loaded into the catheter and advanced through the patient's vasculature to the native valve.

Before these minimally invasive transcatheter valve replacement procedures were developed, the options for most patients needing to their heart valve repaired were limited to significantly invasive surgical replacement procedures. Yet for many patients needing heart valve repair, surgical repair posed a relatively high risk or the patient was not a viable candidate for surgery. With respect to the aortic valve, transcatheter aortic valve replacement (TAVR) procedures have been widely adopted by clinicians throughout the world as an alternative to surgical replacement procedures to treat these high-risk patients having severe aortic stenosis or similar conditions. With many procedures over the decades, TAVR has been shown to improve long term survival of these patients.

Additionally, in recent years, several studies involving both balloon-expandable and self-expanding TAVR prostheses demonstrated that TAVR procedures showed effectiveness for patients with low surgical risk, and in 2019, the U.S. Food & Drug Administration expanded the TAVR indication to include these low-risk patients.

The development of TAVR prostheses, and the related prior art, has focused significantly on the mechanisms and methods for delivering the prosthesis to the native valve, including positioning or re-positioning the prosthesis relative to annulus. However, one challenge practitioners often face during deployment is the ability to align the valve with the existing valve's commissures to create a more natural function of the replacement valve that can bring the patient back to a pre-diseased state. Alignment of commissures in a surgical repair procedure is much easier to achieve than in the minimally invasive transcatheter procedure, with the valve being directed through the patient's vasculature (typically transfemorally) and the practitioner therefore being very removed from the actual deployment site and relying on imaging for positioning of the valve. Even using imaging, the ability to align the commissures can vary broadly by the practitioner's skillset, the duration of the procedure and any other complications, as well as the functionality of the handle, which is the practitioner's only means of controlling the location of the replacement valve during the procedure. This can become an even more pronounced concern in valve-in-valve replacement processes, where a second replacement valve is inserted into an existing damaged or weakened replacement valve and it would be desirable for the second valve's commissures to align with the first valve's for improved outputs. There is a need for a more predictable commissural alignment procedure that simplifies the process and improves the control of the practitioner.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure relates to novel and advantageous systems and methods for commissural alignment of a replacement valve during transcatheter delivery and deployment of the replacement valve within the patient's native or existing valve.

In at least one embodiment, a transcatheter delivery system comprises a catheter assembly comprising a balloon shaft with a balloon mounted onto the balloon shaft. The balloon is in fluid communication with a fluid source for expansion of the balloon from a delivery diameter to a deployed diameter. A valve prosthesis, which may comprise a valve construct attached to an expandable frame, is loaded onto the balloon in a loaded configuration of the valve prosthesis. The valve prosthesis is expandable from the loaded configuration to a deployed configuration by expansion of the balloon from the delivery diameter to the deployed diameter. The catheter assembly further comprises a handle with at least one actuator, wherein the actuator is rotatably engaged with the balloon shaft. In other words, rotation of the actuator rotates the balloon shaft. Rotation of the actuator by an actuator rotation amount in at least a first direction rotates the valve prosthesis in the first direction by a valve rotation amount that is proportional to the actuator rotation amount. Thus, the valve prosthesis can be predictably rotated by the practitioner. In other embodiments, rotation of the proximal end of the balloon shaft that protrudes from the proximal side of the handle may accomplish the valve rotation, rather than via an actuator. In some embodiments, a locking mechanism may lock the balloon catheter in at least an axial position relative to an outer shaft or steerable catheter. This prevents axial motion of the balloon catheter during commissure alignment or other desirable rotation of the balloon catheter when in the locked position. In an unlocked position, axial motion of the balloon catheter relative to the outer shaft or steerable catheter is permitted. In some embodiments, a locking mechanism may lock the balloon catheter in at least an axial position relative to the handle.

In some embodiments, the balloon shaft is a braided shaft. In some embodiments, the balloon shaft has a polymer coating, an elastomeric coating, or combinations thereof. In at least one embodiment, the balloon shaft is coated with a thermoplastic elastomer, such as a polyether block amide known under the tradename of Pebax®.

The ratio of the actuator rotation amount to the valve rotation amount may be a known rotation of any desired amount. In at least one embodiment, the ratio of the actuator rotation amount to the valve rotation amount is a 1:1 ratio. In another embodiment, the ratio of the actuator amount to the valve rotation amount is a 10:8 ratio. In some embodiments, the valve rotation amount may be relatively between about 70-100% of the actuator rotation amount. In other word, radial movement of the actuator results in 70-100% radial movement of the valve. In some embodiments, the valve rotation amount may be relatively between about 50-100% of the actuator rotation amount. In other word, radial movement of the actuator results in 50-100% radial movement of the valve.

The valve prosthesis comprises at least a valve construct having one or more leaflets and an expandable frame. In some embodiments, the valve construct may comprise one or more separate leaflets attached individually to the expandable frame. In some embodiments, the valve construct of the valve prosthesis comprises a sutureless single-piece three-dimensional structure having multiple leaflets. In one embodiment, the sutureless single-piece three-dimensional structure may be made from a single sheet of an acellularized, cross-linked biomaterial, but may be made from other suitable materials in other embodiments. In some embodiments, the expandable frame, which is comprised of a plurality of interconnected struts connected to one another at nodes and may further comprise commissural posts, may have a radiopaque marker to assist with position the valve prosthesis relative to the existing commissures. In some embodiments, the radiopaque marker may be positioned in one of the commissural posts. In other embodiments, a radiopaque marker may be positioned in at least one strut or at least one node of the expandable frame.

The actuator may be rotatable in the first direction, but may also be rotatable in a second direction opposite the first direction. In some embodiments, the handle may further comprise at least one actuator stop which may assist with control of rotation to prevent over and under rotation of the valve prosthesis or to prevent rotation in one of the directions. In still other embodiments, the handle may further comprise a locking member, wherein when the locking member is engaged with the actuator, the balloon shaft cannot rotate.

In some embodiments, a method of transcatheter delivery of a replacement valve to provide commissural alignment with commissures of a patient's existing valve using a catheter handle is provided. The method comprises, in at least one embodiment, loading the replacement valve onto a balloon mounted to a balloon shaft, wherein the balloon shaft is rotatably engaged with an actuator of the catheter handle. The balloon shaft may be a braided shaft. The balloon shaft may also be coated with an elastomeric coating. The method further comprises delivering the replacement valve to a delivery location; rotating the replacement valve by a valve rotation amount to position the replacement valve into an aligned position by rotating the actuator an actuator rotation amount, wherein the actuator rotation amount is proportional to the valve rotation amount; and deploying the replacement valve by expanding the balloon from a delivery diameter to an deployed diameter. In one embodiment, a ratio of the actuator rotation amount to the valve rotation amount is 1:1. In addition to or in replacement of rotation in the first direction, the actuator may be rotatable in a second direction opposition to the first direction. The method, in some embodiments, may further comprise locking the balloon shaft or inner shaft to prevent axial motion, while allowing rotation about the longitudinal axis of the balloon shaft or inner shaft, in the locked position. In the unlocked position, the balloon shaft or inner shaft can move in an axial direction proximally and distally as well as rotate about the longitudinal axis. The method, in other embodiments, may further comprise locking the actuator into a locked position to prevent further rotation of the replacement valve once it is in the aligned position.

In some embodiments, a transcatheter delivery system comprises a catheter assembly having an inner shaft; an outer shaft; and a lock having a locked position and an unlocked position. A valve prosthesis may be loaded onto the inner shaft. Rotation of the inner shaft by a shaft rotation amount in at least a first direction predictably rotates the valve prosthesis in the first direction by a valve rotation amount that is proportional to the shaft rotation amount. The lock has a locked position and an unlocked position, and in the locked position, axial movement of the inner shaft relative to the outer shaft is prevented. In some embodiments, in the locked position, the inner shaft can be rotated in the first direction or in a second direction opposite the first direction. In the unlocked position, the inner shaft can move in an axial direction relative to the outer shaft and the inner shaft can be rotated in at least the first direction. In some embodiments, the transcatheter delivery system further comprises a handle with a locking switch that engages the lock into the locked position and disengages the lock from the locked position into the unlocked position. The inner shaft can be a braided shaft. The valve prosthesis may have at least one alignment marker. In one embodiment, the valve prosthesis has there alignment markers. The alignment markers may be spaced 120 degrees apart in such embodiment, and in other embodiments, the alignment markers may be equally spaced apart. The at least one alignment marker comprises two overlapping serpentine struts, which may form a numeral 8 shape or an "8"-figure shape or a "FIG. 8" shape that may have two openings. The handle may further comprise at least one actuator and in some embodiments may have at least one actuator stop that prevents rotation or movement of the actuator.

In some embodiments, a method of transcatheter delivery of a replacement valve to provide commissural alignment with commissures of a patient's existing valve using a catheter handle is provided. The method comprises loading the replacement valve onto an inner shaft; delivering the replacement valve to a delivery location by advancing the inner shaft within an outer shaft, wherein the inner shaft may be or is in a locked position relative to the outer shaft and a lock in engaged in the locked position; disengaging the lock from the locked position into an unlocked position to permit axial movement of the outer shaft relative to the inner shaft; moving the outer shaft in a proximal direction relative to the inner shaft; engaging the lock into the locked position to prevent axial movement of the inner shaft relative to the outer shaft; rotating the replacement valve by a valve rotation amount to position the replacement valve into an aligned position by rotating the inner shaft a shaft rotation amount, wherein the shaft rotation amount is relative to the valve rotation amount; and deploying the replacement valve.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive. For avoidance of doubt, one or more distinctive features on the frames, including those shown on the figures and others, may be desirable for alignment of the valve as alignment markers, as may be discussed further below

BRIEF DESCRIPTION OF THE DRAWINGS

While the specification concludes with claims particularly pointing out and distinctly claiming the subject matter that is regarded as forming the various embodiments of the present disclosure, it is believed that the disclosure will be better understood from the following description taken in conjunction with the accompanying Figures, in which:

DETAILED DESCRIPTION

Figure 1:
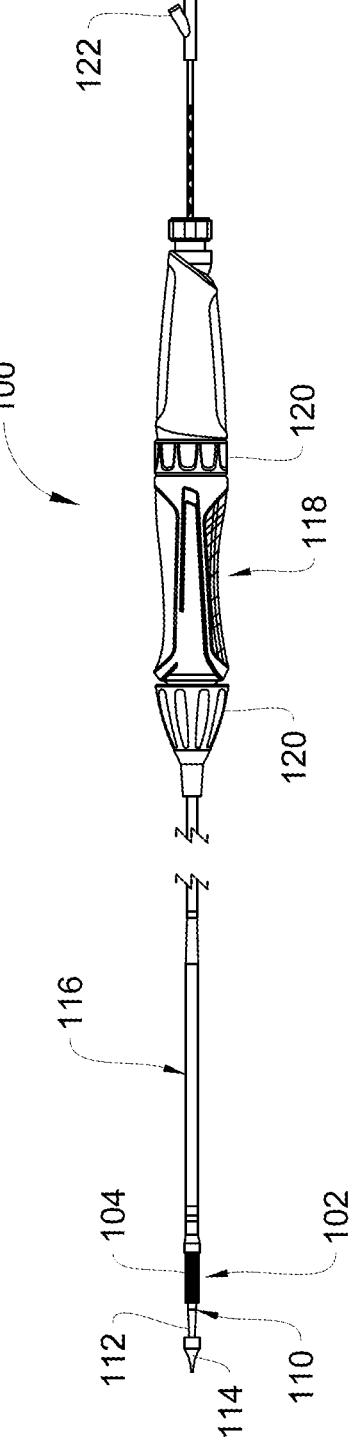
FIG. 1 shows a schematic view of a transcatheter delivery system, according to at least one embodiment of the present disclosure.

The present disclosure describes novel and advantageous valve prosthesis with frames for mounting a valve construct, as well as methods for mounting the valve construct to the frame. While the embodiments and techniques discussed below may be discussed or depicted with respect to aortic valve replacement, it is within the scope of this disclosure that the inventions of the present disclosure may be suitable for use in other valve repair or replacement, such as mitral and tricuspid valves. Further, while the figures and embodiments discussed below may describe an aortic valve that typically have three leaflets, it is within the scope of this disclosure that the inventions of the present disclosure may be suitable for prostheses for use in bicuspid aortic valves.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, and/or components have not been described in detail so as not to obscure the discussion.

FIGS. 1-4 show one embodiment of the transcatheter delivery system 100 of the present disclosure, for delivering the valve prosthesis 102 into the patient's native valve or into an already delivered replacement valve using catheter assembly 103

The valve prosthesis 102 may be a self-expandable valve prosthesis or a balloon expandable valve prosthesis. The valve prosthesis 102 may be designed for either supra-annular placement or intra-annular placement. The valve prosthesis 102 may comprise an expandable frame 104 and a valve construct 106 mounted to the expandable frame. In at least one embodiment, the expandable frame may comprise one or more features of the expandable frames as described in commonly owned and co-pending application PCT/US2021/040592 entitled "Expandable Frame for Improved Hemodynamic Performance of Transcatheter Replacement Heart Valve", which is incorporated by reference herein in its entirety, or in commonly owned and co-pending application PCT/US2021/040596 entitled "Exteriorly Mounted Tissue on Expandable Frame for Improved Hemodynamic Performance," which is incorporated by reference herein in its entirety.

The valve construct 106 may comprise a biomaterial. The biomaterial may comprise one or more of a tissue material, artificial tissue, polymers, plastics, silk, fibrous materials, fabrics, or other woven materials. In some embodiments, the tissue material may be a cross-linked collagen-based biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of commonly owned U.S. Pat. No. 9,205,172, filed on Dec. 21, 2005 and entitled "Implantable Biomaterial and Method of Producing Same," which is incorporated by reference herein in its entirety. In some embodiments, the cross-linked collagen-based biomaterial is treated with the ADAPT® treatment process, which is an anti-calcification treatment process for biomaterials that leaves zero residual DNA and has over ten years of clinical data demonstrating no detectable levels of calcification when used in cardiac surgeries. In some embodiments, the tissue material may be artificial tissue. In some embodiments, the artificial tissue may comprise a single piece molded or formed polymer. In some embodiments, the artificial tissue may comprise polytetrafluoroethylene, polyethylene terephthalate, other polymers, and other polymer coatings. In some embodiments, the valve construct 106 is a single-piece three-dimensional valve construct constructed from a single piece of tissue material, such as the valve described in the disclosure of commonly owned and co-pending U.S. application Ser. No. 16/129,235 and entitled "Replacement Heart Valve with Reduced Suturing," which is incorporated by reference herein in its entirety. In other embodiments, the valve construct may comprise one or more separate leaflets or a unitary structure. In some embodiments, the valve construct may be formed using a mold, may be die cut, or may be constructed using additive manufacturing, including but not limited to melt electrowriting or similar methods.

As shown in FIGS. 1-4, the valve prosthesis 102 is a balloon expandable valve prosthesis, and the catheter assembly 103 may comprise a balloon 110, a balloon shaft 112, a nosecone 114, an outer sheath 116, and a handle 118 with at least one actuator 120 and at least one fluid port 122. The catheter assembly 103 has a distal end 124 and a proximal end 126. The nosecone 114 is generally at the distal end of the catheter assembly, while the handle 118 is in a position near the proximal end 126. For purposes of this disclosure, to move "proximally" means to move in a direction towards the proximal end 126 and to move "distally" means to move in a direction towards the distal end 124.

The balloon shaft 112 may extend from the nosecone 114 proximally to at least the handle 118. The balloon 110 be mounted onto the balloon shaft 112, which is in fluid communication with the handle 118 to allow a fluid or gas delivered from the fluid port 122 to expand the balloon 110 during deployment of the valve prosthesis 102. In addition, the balloon shaft 112 may, in some embodiments, be rotatably engaged with at least one actuator 120. In other embodiments, the balloon shaft 112 may extend proximally from the handle 118, and is rotatable by rotating that portion of the balloon shaft 112 that extends proximally from the handle rather than via an actuator. In at least one embodiment, the balloon shaft 112 is a braided shaft. In some embodiments, the balloon shaft 112 may be a diamond braided shaft. The balloon shaft 112 may be coated with as a polymeric coating, an elastomeric coating, or combinations thereof. In at least one embodiment, the balloon shaft is coated with a thermoplastic elastomer, such as, but not limited to, a polyether block amide known under the tradename of Pebax®. In some embodiments, the balloon shaft may be at least partially covered with a fabric, knit, or other material. In at least one embodiment, the balloon shaft may be at least partially covered with nylon. In some embodiments, the balloon shaft may have an overjacket comprising a polymer, elastomer, fabric, knit or other material.

The outer sheath 116 may be a retractable sheath. In at least one embodiment, the outer sheath 116 may be a steerable outer sheath or steerable outer catheter. In some embodiments, the outer sheath 116 may extend from the handle 118 over the balloon shaft 112, the balloon 110, and the valve prosthesis 102 and abut a proximal end of the nosecone 114 while the valve prosthesis 102 is being delivered through the vasculature to the annulus of the valve for repair or replacement. The outer sheath 116 be engaged with at least one actuator 120 on the handle 118 in order to retract the outer sheath 116 to expose the valve prosthesis 102 and allow for expansion of the valve prosthesis 102 at the delivery site. The outer sheath 116 may be slidably engaged with one actuator 120, which may move the sheath 11 in a proximal direction or distal direction either by rotation of the actuator 120 or sliding action of the actuator 120. In preferred embodiments, the actuator 120 used to retract the retractable outer sheath 116 is not the same actuator used for commissure alignment. The balloon shaft 112 has a loose fit relative to the outer sheath (or, in some embodiments, an intermediate catheter shaft) which permits low friction between the balloon shaft 112 and the outer sheath (or an intermediate catheter shaft) to help prevent or reduce the impact of any windup of the balloon shaft 112.

As shown in FIG. 1, the valve prosthesis 102 is positioned in a loaded configuration relative to the catheter assembly 103. The valve prosthesis 102 may be loaded onto the balloon 104 into the loaded configuration prior to deployment or may be loaded onto the balloon during the delivery procedure, for example, as described in co-pending and commonly owned PCT application entitled "Systems and Methods for Positioning a Valve onto a Catheter During Deployment and Maintaining Such Position" filed on the same day as this application and incorporated herein by reference. In at least one embodiment, in the loaded configuration, the valve prosthesis 102 is positioned over a working section of the balloon 104. In some embodiments, the working section of the balloon 104 is the area of greatest expansion capability of the balloon. With the valve prosthesis loaded onto the balloon, the valve prosthesis 102 is ready for expansion once positioned in a desirable position within the patient's native valve or a failing replacement valve in need of repair. In the loaded configuration, the valve prosthesis 102 is capable of rotating with rotation of the balloon shaft 112 for commissural alignment. In some embodiments, the valve prosthesis 102 may be loaded onto the balloon 104 with a known circumferential orientation relative to the handle 118.

Figure 2:
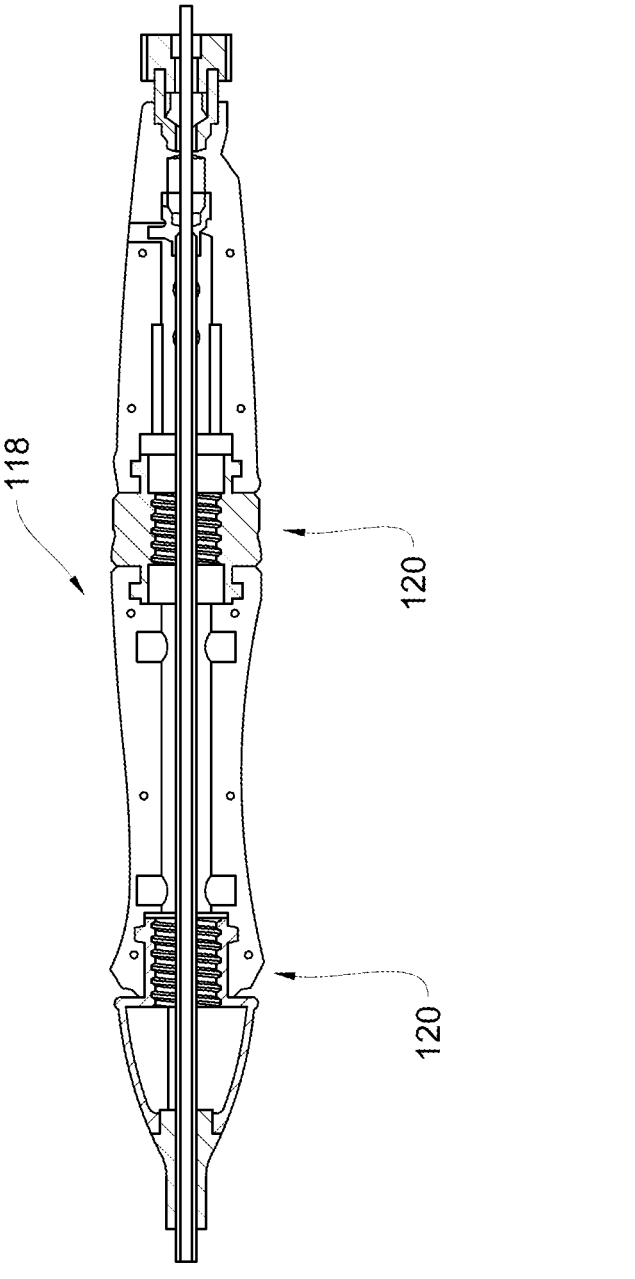
FIG. 2 shows a cross-sectional view of the handle of the transcatheter delivery system shown in FIG. 1.

FIG. 2 shows a cross-sectional view of one embodiment of the handle 118, which has at least one actuator 120 that is rotatably engaged with the balloon shaft 112. Rotation of the actuator 120 may, in some embodiments, permit rotation of the balloon shaft 112, which allows the valve prosthesis 102 to rotate about the longitudinal axis of the balloon shaft 112. The actuator 120 may be at or near the proximal end of the handle, in the middle of the handle, or at or near the distal end of the handle. The actuator 120 may be a spinning wheel, knob, or a switch. Where the actuator 120 is a switch, the switch may have two or more positions. In some embodiments, where the actuator is a switch, the switch may have three positions and in one embodiment, the switch is a rotary switch with three positions that may be spaced 120 degrees apart from one another. In some embodiments, the switch may have four or more positions. In some embodiments, the actuator 120 may only permit stepped, predetermined rotation. In some embodiments, the actuator 120 is only permitted to rotate in one direction. In some embodiments, the actuator 120 can rotate in a first direction and a second direction. In some embodiments, the actuator 120 may have an actuator stop that prevents full rotation of the actuator 120 so that the balloon shaft and thus the valve prosthesis can only rotate a certain number of degrees. This limited sweep angle may be 60 degrees, 90 degrees, 120 degrees, or 180 degrees. Rotation of the actuator 120, in some embodiments, results in rotation of the balloon shaft 112 and therefore rotation of the valve prosthesis 102. Although this paragraph describes using an actuator to rotate the balloon shaft, the balloon shaft may be rotated by hand by the practitioner. In other words, the balloon shaft is rotatable relative to the outer shaft or steerable catheter, or may be rotatable relative to an inner lumen of the handle. More particularly, the balloon shaft may extend proximally from the proximal end of the handle and this portion of the balloon shaft may is rotatable in order to rotate the valve prosthesis 102.

In some embodiments, the handle may further comprise one or more deflection actuators that rotatably engage with a pull wire within the steerable catheter shaft to deflect the catheter during delivery of the valve to the patient's native valve or a failing replacement valve in need of repair.

In some embodiments, as shown in FIG. 2, the handle 118 may further comprise at least one actuator lock 130 that is configured, in some embodiments, to prevent rotation of the actuator 120 (and therefore prevent rotation of the balloon shaft 112) or, in some embodiments, the at least one actuator lock 130 is configured to prevent axial movement of the balloon shaft 112 relative to the steerable catheter 116 during delivery. In other words, the handle 118 may comprise a rotational lock and/or an axial lock. In some preferred embodiments, the actuator lock Engagement of at least one of the locks 130 may, in some embodiments, prevent axial motion of the steerable catheter relative to the balloon catheter. Disengagement of at least one of the locks 130 may, in some embodiments, permit the steerable catheter to be withdrawn proximally relative to the balloon catheter and valve prosthesis. In some embodiments where the lock prevents axial motion, rotation of the balloon catheter and valve prosthesis may still be possible regardless of whether such axial lock is engaged or disengaged. FIG. 2 depicts one embodiment of the lock 130 comprising a lock switch 132 and a collet 134 to permit or prevent at least one of the axial movement of the balloon catheter relative to the steerable catheter or the handle, or rotation of the balloon catheter of the delivery device. In some other embodiments, the lock may comprise one or more of a physical snap, screw, hard stop, pull, or push locking mechanism contained within the handle. In some embodiments, the lock may contain mating components on both the handle and balloon catheter. In such embodiments, the lock may comprise a handle locking component and a balloon catheter locking component. The handle locking component may interact with the balloon catheter locking component via a mechanical stop, seal, o-ring, bladder, collet, or similar mechanic to lock and unlock rotation. Thus when the handle locking component is engaged with the balloon catheter locking component, axial movement of the balloon catheter may be permitted or prevented.

In some embodiments, having at least one rotational lock, when the rotational lock is engaged, rotational movement of the balloon shaft can be prevented and when disengaged, rotational movement of the balloon shaft is permitted. The rotational lock can be engaged again, once the practitioner is satisfied that commissural alignment has been achieved, in order to prevent further rotation upon delivery. In at least one embodiment, the rotational lock must be engaged prior to inflation of the balloon.

In some embodiments, the lock may comprise of a physical snap, screw, hard stop, pull, or push locking mechanism contained within the catheter handle. In some embodiments, the lock may contain interactive components on both the handle and balloon catheter. A catheter lock may interact with the balloon catheter via a mechanical stop, seal, o-ring, bladder, collet, or similar mechanic to lock and unlock rotation. In some embodiments, the actuator locking mechanism may comprise of a physical snap, screw, hard stop, pull, or push locking mechanism contained within the catheter handle. In some embodiments, the actuator locking mechanism may contain interactive components on both the handle and balloon catheter. The catheter handle locking mechanism may interact with the balloon catheter via a mechanical stop, seal, o-ring, bladder, collet, or similar mechanic to lock and unlock rotation.

In some embodiments, the handle may further comprise one or more deflection actuators that rotatably engage with a pull wire in the steerable catheter shaft to deflect the catheter during delivery of the valve to the patient's native valve or a failing replacement valve in need of repair.

In some embodiments, rotation of the valve is controlled by the catheter handle. In one embodiment, the handle interacts with the balloon catheter to translate rotation and achieve alignment of the valve. This interaction can introduce movement via a button, switch, turn dial, turn wheel, or any other means of translating manual adjustments to the rotating the valve. In some embodiments the balloon catheter and handle may engage and disengage from one another to achieve rotation of the valve. The engagement between components may comprise of a physical snap, screw, hard stop, pull, or push locking mechanism contained within the catheter handle. The catheter handle locking mechanism may interact with the balloon catheter via a mechanical stop, seal, o-ring, bladder, collet, or similar mechanic to lock and unlock rotation.

Figures 3A, 3B:
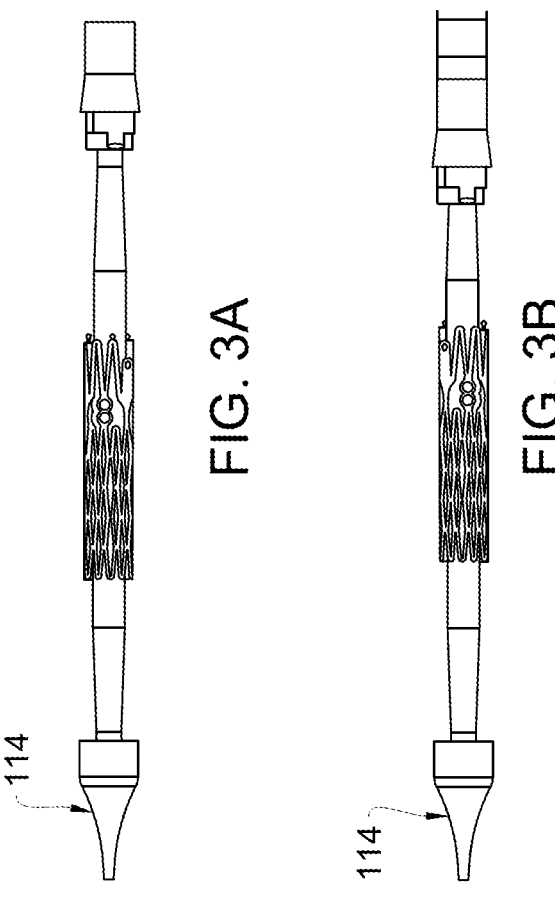
FIG. 3A-3B show the valve prosthesis, which is loaded onto the transcatheter delivery system shown in FIG. 1, rotated from a first position shown in FIG. 3A to a second position shown in FIG. 3B.

Rotation of the commissural alignment actuator 120 by an actuator rotation amount in a first direction predictably rotates the valve prosthesis in the first direction by a valve rotation amount that is proportional or relative to the actuator rotation amount. The ratio of the actuator rotation amount to the valve rotation amount may be a known rotation of any desired amount. In at least one embodiment, the ratio of the actuator rotation amount to the valve rotation amount is a 1:1 ratio. In another embodiment, the ratio of the actuator amount to the valve rotation amount is a 10:8 ratio. In some embodiments, the valve rotation amount may be relatively between about 70-100% of the actuator rotation amount. In other word, radial movement of the actuator results in 70-100% radial movement of the valve. In one embodiment, the valve rotation is introduced by rotation of a handle spin wheel, knob, or switch. In one embodiment, the rotation of the valve is introduced by rotating the balloon catheter via the proximal end. FIGS. 3A-3B demonstrate this rotation, according to one embodiment.

As shown in FIG. 3A-3B, the frame 104 of the valve prosthesis has at least one alignment marker 150. In some embodiments, the alignment marker may be positioned on a commissural post of the frame. As shown in FIGS. 3A-3B, the alignment marker 150 comprises two overlapping serpentine struts 153, 154 that may form an "8"-figure shape with two openings. In some embodiments, the alignment marker 150 may further comprise a radiopaque marker, which may be positioned within a hole or opening of the alignment marker or about a strut or a commissural post 155 of the frame. In some embodiments, the radiopaque marker may be positioned on a commissural post of the frame. In other embodiments, the alignment marker may comprise a series of slits in a pattern within one or more of the struts or posts of the frame. For example, the slits may form a lowercase "d" on one of the struts or posts of the frame but the pattern may also form a capital "D" or any other suitable or desirable configuration. In other embodiments, the alignment marker may comprise a hole, a disc, a slot, or other alignment feature. In some embodiments, the valve prosthesis 102 has a single alignment marker 150. In some embodiments, the valve prosthesis 102 may have more than one alignment marker. The valve prosthesis 102 may have three alignment markers, each equally spaced apart around the circumference of the valve prosthesis 102. In some embodiments, the alignment markers may be identical and in other embodiments, the alignment marker may differ in shape from a circumferentially adjacent marker. The alignment marker 150 may be visually identifiable to a practitioner during the delivery procedure, and thus the practitioner can rotate the actuator by a known amount to achieve commissural alignment of the valve.

In some embodiments, a practitioner can use particular imaging views to align the alignment marker 150 with the commissures on the patient's native valve or in a failing replacement valve. Imaging may include x-ray, computed tomography, fluoroscopy, or other suitable imaging techniques. Where the alignment marker comprises overlapping serpentine struts 153, 154 that may form an "8"-figure shape with two openings, and when performing an aortic valve repair, the alignment marker 150 can be aligned with the nadirs of each aortic cusp or commonly referred to as the belly of the leaflet. By aligning with the nadirs of the leaflets, the commissure posts of the valve prosthesis are ensured to be aligned with the commissures of the native aortic leaflets (or in the case of a failing repair valve during valve-in-valve repair, the repair leaflets of the failing repair valve). To aid in alignment, the patient may receive a pre-procedural computed tomography (CT) scan. Analysis of this CT scan provides the implanting practitioner with fluoroscopic angles that align with the annular plane. The annular plane is defined by the three nadirs of the aortic cusps. Generally there are two commonly used views: a 3-cusp view and a cusp overlap view. In the 3-cusp view, the alignment marker 150 may be identified in the middle of the image so that it aligns with the nadir of, for example, the right coronary cusp. When a properly oriented valve prosthesis is viewed from the cusp overlap view, two of the alignment markers 150 will be superimposed or overlap one another, typically near the right coronary ostia and the left coronary ostia. A third alignment marker 150, positioned at 120 degrees from the other alignment markers, and associated with the non-coronary cusp, will be difficult to observe since the third alignment marker 150 is 90 degrees from the plane of viewing. This is particularly true where the alignment marker comprises overlapping serpentine struts 153, 154 that may form an "8"-figure shape with two openings, but may also be true for other alignment marker configurations. While this paragraph discusses imaging and positioning with respect to an aortic valve repair or replacement procedure, it is within the scope of this invention to apply similar techniques to alignment of a valve prosthesis in mitral or tricuspid valve repair or replacement procedures.

Figures 4A, 4B:
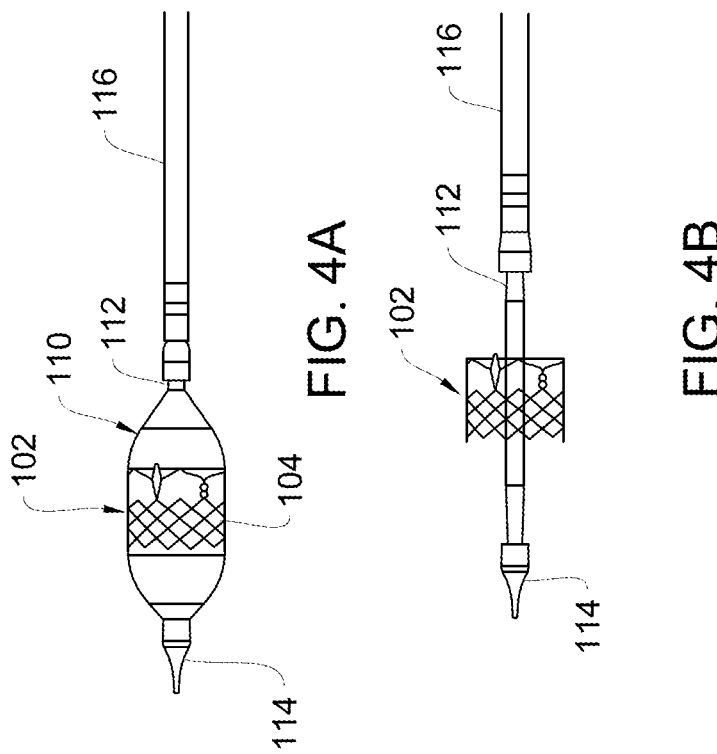
FIG. 4A shows the valve prosthesis shown in FIGS. 3A-3B expanded to an expanded state for deployment, according to at least one embodiment of the present disclosure.
FIG. 4B shows the valve prosthesis of FIG. 4A in the deployed state with the balloon deflated and the delivery system ready for withdrawal.

Once the valve is in the desired position, as shown in FIG. 4A-4B, the valve prosthesis can then be expanded from the loaded configuration to an expanded configuration by expanding the balloon. The balloon can then be collapsed and the transcatheter delivery system can be withdrawn from the vasculature.

In some embodiments, such as the embodiment shown in FIGS. 1-4, the transcatheter delivery system 100 starts or is introduced into the body with the valve prosthesis in a loaded configuration (in other words, with the valve prosthesis crimped onto the balloon) between the nosecone and the proximal end of the balloon. In at least one embodiment, a distal portion (including the distal end) of the steerable catheter covers at least the proximal end of the valve prosthesis in the loaded configuration. At this point during the procedure, at least one of the actuator locks on the handle is engaged, and in particular, the axial actuator lock may be engaged. Additionally, in some embodiments, the proximal end of the valve prosthesis, and more particularly the proximal crowns or end of the crimped valve prosthesis, are engaged in the loaded configurations with retention features on the distal end of the steerable catheter. The retention features may be nubs, lugs, posts, fingers, rods or other similar structures that engage with openings between struts at or near the proximal end of the valve prosthesis and in other embodiments may be slots, holes or openings that mate with one or more struts at or near the proximal end of the valve prosthesis. In some embodiments, the distal end of the crimped valve may be retained, captured or covered by the proximal portion or end of the nosecone. In at least one embodiment, the distal crowns or distal end of the crimped valve may be retained, captured or covered by the proximal portion or end of the nosecone. While the valve prosthesis is in the loaded configuration and during delivery of the valve prosthesis, at least one of the actuator locks may be engaged. For example, the axial actuator lock may be engaged in one embodiment, and in other embodiments the rotational actuator lock may be engaged or in still other embodiments both the axial actuator and the rotational actuator lock may be engaged. The valve prosthesis remains in the loaded configuration during delivery, including navigation around the arch and across the native aortic valve or failing replacement device, with the user able to apply deflection to the steerable catheter as needed for navigation. Once the distal end of the catheter assembly is across the valve, the axial lock may be disengaged, and the balloon catheter shaft may be advanced. The retention mechanisms hold the prosthesis in position relative to the steerable catheter. The balloon is advanced until the prosthesis is on the middle, or working section, of the balloon. Once in this position, the retention mechanisms are disengaged, decoupling the steerable catheter from the prosthesis. The steerable catheter may then be withdrawn, exposing the proximal end of the inflation balloon. The axial lock is then re-engaged, and commissure alignment is performed by rotation of the balloon catheter. Once rotational (commissural) alignment is achieved and the valve is positioned at the correct depth of implant, the device is ready for deployment. High rate pacing is initiated, the balloon is expanded, which anchors the prosthesis into the native aortic valve. The balloon is then deflated and high rate pacing is turned off. The catheter assembly is then withdrawn from the body, leaving the valve prosthesis in place.

Figure 5:
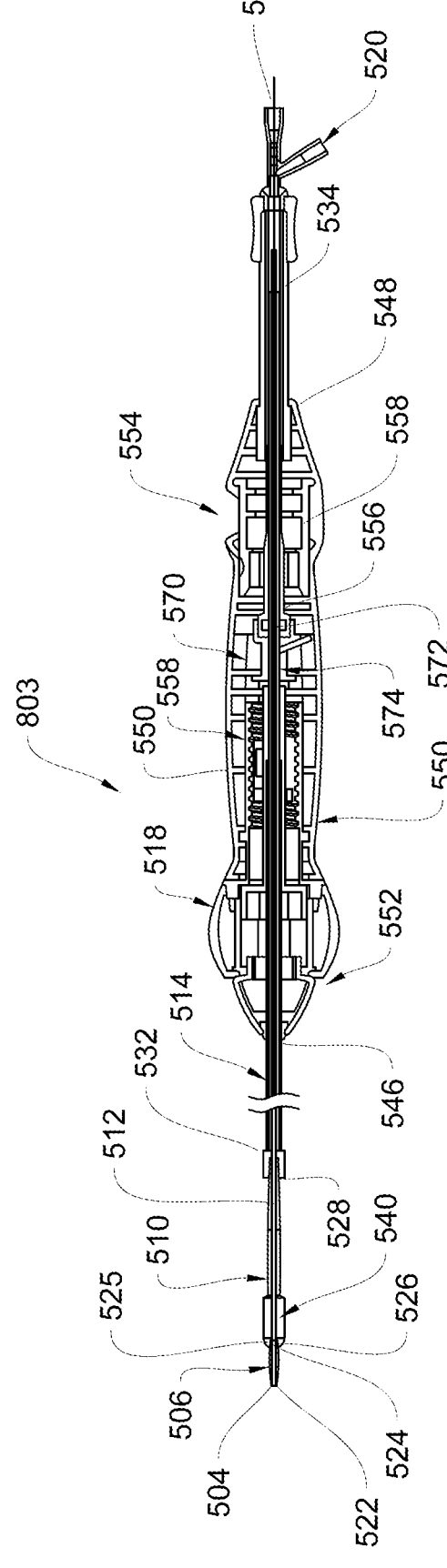
FIG. 5 is a cross-sectional view of another embodiment of the catheter assembly of the transcatheter delivery system, according to at least one embodiment of the present disclosure.
Figure 6:
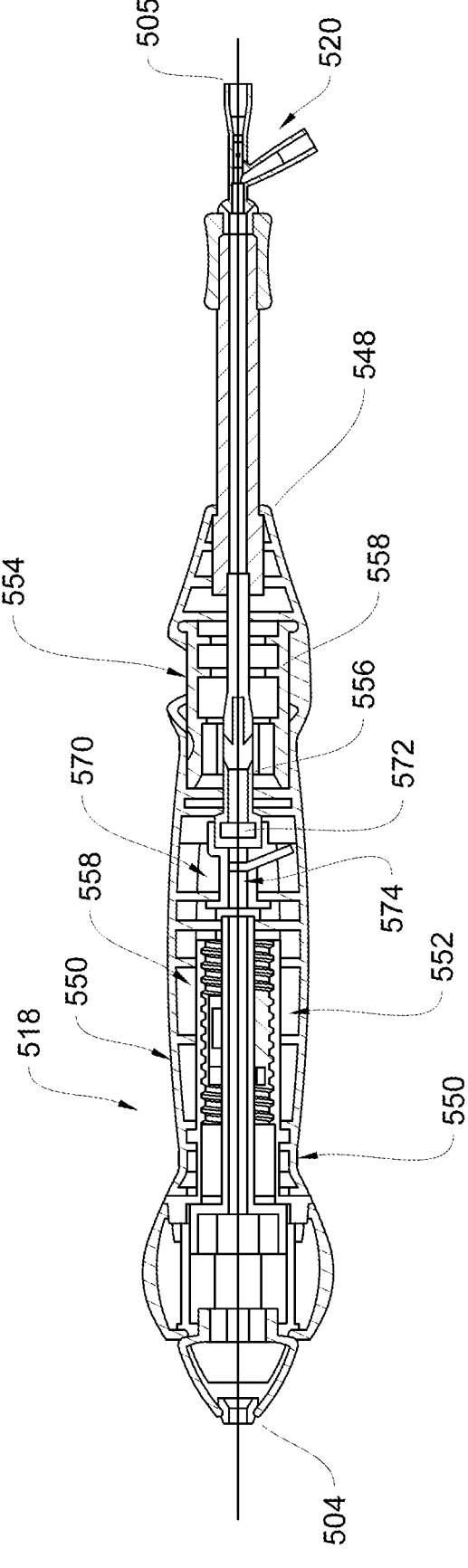
FIG. 6 is a cross-sectional view of the handle shown in FIG. 5.

FIG. 5 shows a cross-sectional views of the transcatheter delivery system 500 according to one or more embodiments of the claimed invention, and FIG. 6 shows a cross-sectional view of an embodiment the handle 518 of the transcatheter delivery system 500 shown in FIG. 5. The transcatheter delivery system 500 comprises In at least one embodiment, the transcatheter delivery system 500 starts or is introduced to the body with the valve prosthesis in a loaded configuration. In the loaded configuration, the valve prosthesis is crimped or otherwise loaded onto the balloon and, in some embodiments, the distal end of the steerable catheter may cover the proximal end of the valve prosthesis. In some embodiments, the valve prosthesis is crimped onto the balloon proximally to the nosecone, and in still other embodiments, the valve prosthesis is crimped proximally to a puffed portion of the balloon. In the loaded configuration, the axial lock on the handle may be engaged. The transcatheter delivery system stays in this loaded configuration during delivery navigation around the arch and across the native aortic valve, with the user able to apply deflection to the system as needed for navigation. Once across the valve and in the desired axial position for deployment, the axial lock is disengaged, and the steerable catheter is withdrawn, exposing the proximal end of the inflation balloon. The axial lock is then re-engaged, and commissure alignment is performed by rotation of the balloon catheter. Once rotational (commissural) alignment is achieved and the valve is positioned at the correct depth of implant, the device is ready for deployment. High rate pacing May then initiated and the balloon is expanded, thereby expanding the valve prosthesis. The expansion of the balloon may permit anchoring of which anchors the prosthesis into the patient's native valve or within a failing replacement valve in need of repair. The balloon is then deflated and high rate pacing, if used, may then be turned off. The delivery system device may then be withdrawn from the body, leaving the valve prosthesis in place in its delivery position within the native valve or the failing replacement valve.

The transcatheter delivery system in FIG. 5 comprises a catheter assembly 503 having a distal end 504 and a proximal end 505. The catheter assembly 503 comprises a nosecone 506, a balloon 510, an inner shaft 512, an outer shaft 514, a handle 518, and a fluid port 520 in communication with the balloon 510 for expanding and deflating the balloon using fluids or gases. The nosecone 506 has a distal end 522 and a proximal end 524. In some embodiments, the nosecone 506 is solid and in other embodiments, the nosecone 506 may be expandable or inflatable. The nosecone 506 may comprise, in some embodiments, a polymer, rubber, plastic, elastomer, or other material. The proximal end 524 of the nosecone 506 may be connected to a distal end 525 of the inner shaft 512. The inner shaft 512 may have one or more marker bands or radiopaque markers between the nose cone 506 and the handle 518 as described further below. The balloon 510 has a distal end 526 and a proximal end 528, where the distal end 526 in at least one embodiment abuts the proximal end 524 of the nosecone 506. The balloon 510 may have a puffed portion 540 near the distal end 526. The outer shaft 514 may be a steerable shaft, a retractable shaft, or an intermediate shaft. The outer shaft 514 has a greater diameter than the inner shaft 512. The outer shaft 514 may have a distal end 532 and a proximal end 534. In some embodiments, the outer shaft 514 may have a radiopaque marker at the distal end 532. The handle 518 has a distal end 546 and a proximal end 548. As shown in FIG. 5, the inner shaft 512 may itself extend or rotatably extend proximally from the proximal end 548 of the handle 518. FIG. 6 depicts one embodiment of the handle 518, which may comprise a housing 550 and, in at least one embodiment, an actuator 552. In some embodiments, the actuator 552 may be near the distal end 546, and in other embodiments the actuator 552 may be located elsewhere along the housing 550. The actuator may be used for deflection of the outer sheath or, in some embodiments, may be used for rotation of the inner shaft. In some embodiments, the handle 518 may further comprise a pull wire ring assembly 554 for deflecting comprising a pull wire 556 engaged with the outer shaft or the steerable shaft at one end and a ring 558 at the other end. The pull wire ring assembly 554 may be engaged with the actuator 552. In addition to the pull wire ring assembly 554, or in an alternative to the pull wire ring assembly 554, the handle 518 may comprise rack and pinion gear assembly 558 for deflection of the outer shaft or the steerable shaft. In some embodiments, the handle 518 may further comprise a lock 570 comprising a locking collet 572 and a lock switch 574 to permit or prevent at least one of the axial movement of the balloon catheter relative to the steerable catheter or the handle, or rotation of the balloon catheter of the delivery device. In some embodiments, the lock switch 574 may be activated, engaged, or disengaged by rotating the switch from a first position to a second position to put the lock 570 in the locked or unlocked position. In other embodiments, the lock switch 574 may be activated, engaged or disengaged by pulling the lock switch proximally (or pushing it distally) to put the lock 570 in the locked or unlocked position.

While the above disclosure is described with respect to a balloon expandable valve, the concepts and features are similarly applicable to self-expanding valves. In some embodiments, modifications to the systems and methods described above for balloon expandable valves may be needed for self-expanding valves as the means for deployment of a balloon expandable valve and a self-expanding valve differ. For example, self-expanding valves generally do not require a balloon for expansion of the valve prosthesis.

Figure 7:
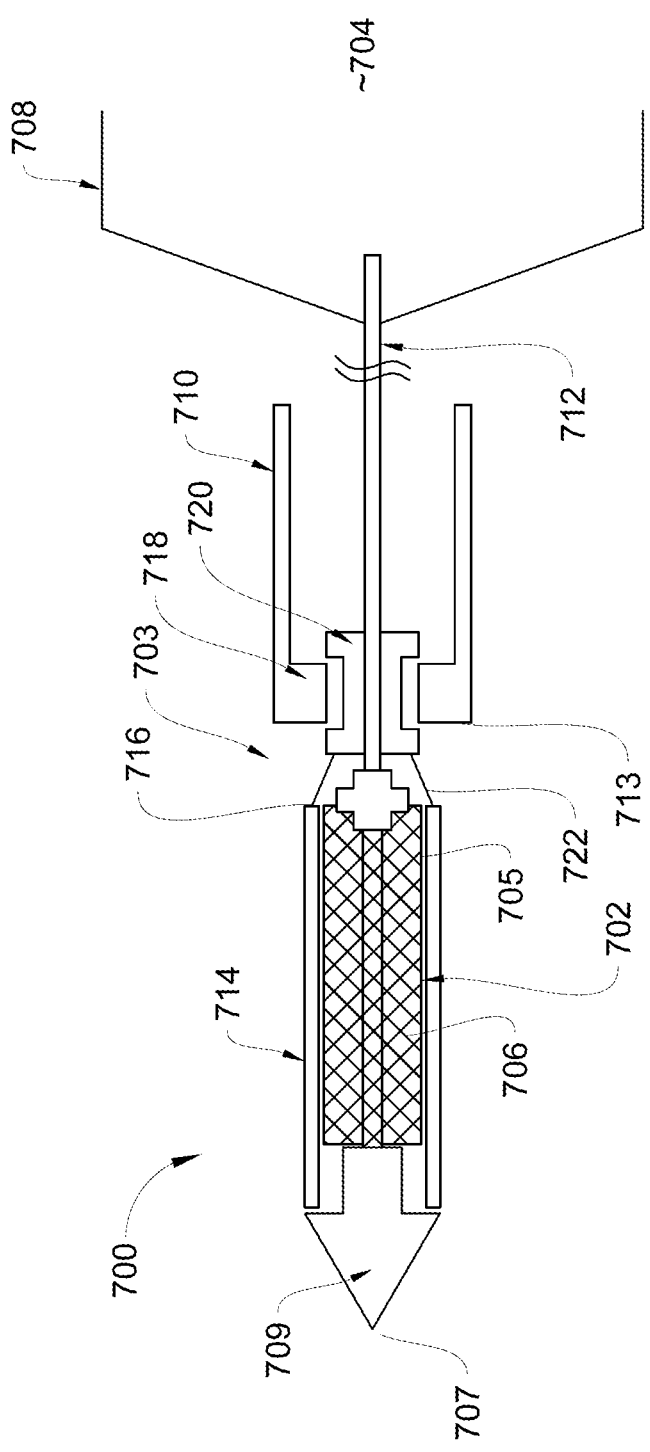
FIG. 7 is a schematic of another embodiment of a transcatheter delivery system, where the valve prosthesis is a self-expanding valve.

FIG. 7 shows a schematic of one embodiment of a transcatheter delivery system 700 comprising a self-expanding valve prosthesis 702 and a catheter assembly 703 for commissural alignment of the self-expanding valve prosthesis 702 during its deployment and delivery. The valve prosthesis 702 is similar to the valve prosthesis discussed above and comprises a frame 705 and a valve construct 706 attached to the frame 705. The catheter assembly 703 has a proximal end 704 and a distal end 707, and the catheter assembly 703 comprises at least a handle 708 near the proximal end 704, a nosecone 709 near the distal end 707, a steerable outer shaft 710, and an inner shaft 712 extending between the distal tip 709 and the handle 708. The steerable outer shaft 710 has a distal end 713. In some embodiments, the catheter assembly 703 further comprises a retractable sheath 714 between the inner shaft 712 and the steerable outer shaft 710. In some embodiments, the retractable sheath 714 may extend distally from the distal end 713 of the steerable outer shaft 710 to cover the valve prosthesis 702 in the loaded configuration. In other embodiments, the retractable sheath 714 may extend proximally from the nosecone 709 to cover the valve prosthesis 702 in the loaded configuration. In still further embodiments, the retractable sheath may comprise a split sheath with elements on both the steerable outer shaft and the inner shaft to cover the valve in the loaded configuration.

In some embodiments, the inner shaft 712 has one or more valve retention features 716, such as pegs, lugs, knobs, rods, fingers, or other extensions, that are releasably engaged with the valve prosthesis 702 to hold the valve prosthesis 702 in axial and/or rotational position relative to the inner shaft 712. In some embodiments, a control mechanism within the handle may be connected to the valve retention features to rotate or retract the valve retention features to release the valve. In other embodiments, the valve prosthesis 702 may be released from the valve retention features 716 upon expansion of the valve prosthesis. The valve retention features 716 may also be configured to permit a desired expansion profile of the valve prosthesis 702 and/or a desired delivery profile of the valve prosthesis 702 during navigation around the arch.

In some embodiments, the steerable outer shaft 710 may have sheath retention features 718 at or near a distal end of the steerable outer shaft 710. The sheath retention features 718 allow for rotation of the inner shaft 712 relative to the steerable outer shaft 710.

The valve prosthesis 702, in a loaded configuration, is disposed about the inner shaft 712 and sheathed by either the steerable outer shaft 710 or the retractable sheath 714 covers the valve prosthesis 702 to prevent expansion. The system 700 remains in this sheathed configuration while navigating around the arch during delivery and across the native valve or failing replacement valve, with the practitioner able to apply deflection to the system as needed for such navigation, including by using deflection actuators on the handle as described above. Once across the patient's native valve or failing replacement valve and the practitioner is ready for deployment of the valve prosthesis, the inner shaft 712 may be rotated to align the valve prosthesis 702 with the commissures of the native valve or the failing replacement valve much like the balloon shaft as described above. More specifically, the inner shaft 712 may be rotated to align the commissural posts of the valve prosthesis 702 with the commissures of the native valve or the failing replacement valve. When the valve is aligned in position for deployment, the steerable outer shaft 710 and/or the retractable sheath 714 can be withdrawn, which causes the self-expanding frame of the valve prosthesis 702 to expand outwardly as the sheath 714 to anchor the valve prosthesis 702 within the native anatomy or within the failing replacement valve. The valve prosthesis 702 can be released from the one or more valve retention features 716 on the inner shaft 712, and the releasing may occur by the mechanical expansion of the valve prosthesis 702 or by releasing a control mechanism on the handle that causes the valve retention features 716 to retract within the inner shaft 712. Once the valve prosthesis 702 is fully deployed within the patient's native valve or failing replacement valve, the catheter assembly 703 may then be removed from the patient's body.

In at least one embodiment, whether a balloon expandable valve prosthesis or a self-expanding valve prosthesis, the valve prosthesis is first in a loaded configuration or crimped configuration on the inner shaft. When beginning to advance the from the access site to the top of the descending thoracic aorta, in an aortic valve repair procedure, the inner shaft may be locked in a relative position with the outer shaft to prevent axial movement of the inner shaft relative to the outer shaft. The delivery system may then be advanced around the aortic arch, again in an aortic valve repair procedure. Articulation of the steerable catheter, using one or more actuators on the handle may be used to deflect or steer the delivery system through the vasculature atraumatically. While advancing under fluoroscopic visualization, the practitioner may turn one or more of the actuators in a first or second direction to deflect or steer the delivery system through the vasculature. When the practitioner is ready, the inner shaft may be unlocked relative to the outer shaft, allowing the steerable catheter may be pulled proximally to expose the remainder of the balloon and to release the proximal end (or the proximal outflow crowns) from the flared portion of the steerable catheter. To unlock the inner shaft relative to the outer shaft, a locking switch may be turned from the locked position to an unlocked position to disengage the lock or, in some embodiments, a lock near the proximal end of the handle may be pulled proximally (or pushed distally in other embodiments) to disengage the lock and permit axial movement of the inner shaft relative to the outer shaft. In at least one embodiment, a proximal-most radiopaque marker band on the inner shaft indicates to the practitioner how far in the proximal direction the steerable catheter or outer shaft should be pulled. Once the steerable catheter or outer shaft is in the desired position, the lock can be engaged again to prevent axial movement of the inner shaft relative to the outer shaft. The practitioner can then rotate the valve by rotating the inner shaft, either by hand or with an actuator on the handle, to align the commissures on the valve prosthesis with the patient's native valve or failing replacement valve. Once centered or in a position desired by the practitioner, and in some embodiments once aligned with the commissures, any further minor adjustments may be made by moving the catheter assembly proximally or distally relative to the guidewire or applying small deflections to the catheter assembly. The valve prosthesis can then be expanded, pushing aside the native aortic leaflets and/or the failing replacement valve's leaflets and engaging with the patient's current annulus. Where the valve prosthesis is a balloon expandable valve, the balloon may then be deflated by releasing fluid, gas, or air pressure. The valve prosthesis begins to function. In some embodiments, the lock can be disengaged again and the inner shaft can be pulled back proximally into the outer shaft or steerable catheter. The lock can then be engaged again to prevent relative axial movement of the shafts, and the inner shaft and the outer shaft or steerable catheter can be simultaneously withdrawn. In other embodiments the outer shaft or steerable catheter can be pulled out from the patient's vasculature separately from the inner shaft.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention.

What is claimed is:

1. A transcatheter prosthetic heart valve delivery system comprising:
   a balloon shaft;
   a balloon mounted onto the balloon shaft, the balloon having a delivery diameter, the balloon in fluid communication with a fluid source for expansion of the balloon from the delivery diameter to a deployed diameter; and
   a handle comprising an actuator engaged with the balloon shaft,
   wherein rotation of the actuator by an actuator rotation amount in a first direction predictably rotates the balloon in the first direction by a balloon rotation amount that is proportional to the actuator rotation amount.

2. The transcatheter prosthetic heart valve delivery system of claim 1, wherein a ratio of the actuator rotation amount to the balloon rotation amount is 1:1.

3. The transcatheter prosthetic heart valve delivery system of claim 1, further comprising a valve prosthesis loaded onto the balloon wherein the valve prosthesis comprises a valve construct attached to a frame.

4. The transcatheter prosthetic heart valve delivery system of claim 3, wherein the valve construct comprises a sutureless single-piece three-dimensional structure with three leaflets molded into the sutureless single-piece three-dimensional structure.

5. The transcatheter prosthetic heart valve delivery system of claim 3, wherein the frame includes at least one radiopaque marker.

6. The transcatheter prosthetic heart valve delivery system of claim 5, wherein the at least one radiopaque marker is positioned on a commissural post of the frame.

7. The transcatheter prosthetic heart valve delivery system of claim 6, wherein the at least one radiopaque marker is positioned onto at least one of a node or a strut adjacent to the commissural post.

8. The transcatheter prosthetic heart valve delivery system of claim 1, wherein the handle further comprises at least one actuator stop.

9. The transcatheter prosthetic heart valve delivery system of claim 1, wherein the handle further comprises a locking member, wherein when the locking member is engaged with the actuator, the balloon shaft cannot rotate.

10. The transcatheter prosthetic heart valve delivery system of claim 1, wherein the actuator is rotatable in the first direction and in a second direction opposite the first direction.

11. A prosthetic heart valve transcatheter delivery system comprising:
   an inner shaft;
   a balloon coupled to a distal end portion of the inner shaft;
   an outer shaft; and
   a lock having a locked position and an unlocked position,
   wherein rotation of the inner shaft by a shaft rotation amount in a first direction predictably rotates the balloon in the first direction by a balloon rotation amount that is proportional to the shaft rotation amount, and
   wherein, when the lock is in the locked position, axial movement of the inner shaft and balloon relative to the outer shaft is prevented.

12. The prosthetic heart valve transcatheter delivery system of claim 11, further comprising a handle with a locking switch that engages the lock into the locked position.

13. The prosthetic heart valve transcatheter delivery system of claim 12, wherein the locking switch disengages the lock from the locked position into the unlocked position.

14. The prosthetic heart valve transcatheter delivery system of claim 11, wherein in the locked position, the inner shaft can be rotated in the first direction.

15. The prosthetic heart valve transcatheter delivery system of claim 14, wherein in the locked position, the inner shaft can be rotated in a second direction.

16. The prosthetic heart valve transcatheter delivery system of claim 11, wherein in the unlocked position, the inner shaft can move in an axial direction relative to the outer shaft and the inner shaft can be rotated in at least the first direction.

17. The prosthetic heart valve transcatheter delivery system of claim 11, wherein the inner shaft is a braided shaft.

18. The prosthetic heart valve transcatheter delivery system of claim 11, further comprising a valve prosthesis comprising at least one alignment marker.

19. The prosthetic heart valve transcatheter delivery system of claim 18, wherein the valve prosthesis comprises at least three alignment markers.

20. The prosthetic heart valve transcatheter delivery system of claim 18, wherein the at least one alignment marker comprises two overlapping serpentine struts forming a numeral 8 shape defining two openings containing radiopaque markers.

* * * * *